United States Patent
Thaning

(10) Patent No.: US 9,023,320 B2
(45) Date of Patent: May 5, 2015

(54) METHOD OF PRODUCING A COMPOSITION, COMPOSITION AND ITS USE

(75) Inventor: Mikkel Thaning, Oslo (NO)

(73) Assignee: GE Healthcare AS, Oslo (NO)

( * ) Notice: Subject to any disclaimer, the term of this patent is extended or adjusted under 35 U.S.C. 154(b) by 2175 days.

(21) Appl. No.: 11/572,671

(22) PCT Filed: Jul. 28, 2005

(86) PCT No.: PCT/NO2005/000281
§ 371 (c)(1),
(2), (4) Date: Jan. 25, 2007

(87) PCT Pub. No.: WO2006/011809
PCT Pub. Date: Feb. 2, 2006

(65) Prior Publication Data
US 2008/0213186 A1    Sep. 4, 2008

(30) Foreign Application Priority Data
Jul. 30, 2004  (NO) .................................. 20043229

(51) Int. Cl.
| A61B 5/055 | (2006.01) |
| A61K 49/18 | (2006.01) |
| C07D 519/00 | (2006.01) |
| G01N 24/00 | (2006.01) |
| A61K 49/10 | (2006.01) |

(52) U.S. Cl.
CPC ............ *A61K 49/1815* (2013.01); *G01N 24/00* (2013.01); *A61K 49/10* (2013.01); *C07D 519/00* (2013.01)

(58) Field of Classification Search
None
See application file for complete search history.

(56) References Cited

U.S. PATENT DOCUMENTS

| 6,278,893 B1 * | 8/2001 | Ardenkjaer-Larson et al. .............................. 600/420 |
| 2003/0194810 A1 * | 10/2003 | Dotsch et al. .................... 436/18 |

FOREIGN PATENT DOCUMENTS

| WO | 91/12024 | 8/1991 |
| WO | 96/39367 | 12/1996 |
| WO | WO 9639367 A1 * | 12/1996 |
| WO | 97/09633 | 3/1997 |
| WO | 98/39277 | 9/1998 |
| WO | 99/35508 | 7/1999 |
| WO | 02/37132 | 5/2002 |

OTHER PUBLICATIONS

Gibson, M., "Pharmaceutical Preformulation and Formulation: A Practical Guide from . . . ", 2001, CRC Press, Edition 1, p. 333.*
Sombra, L.L., et al., "Assessment of trace aluminum content . . . ", 2003, Journal of Pharmaceutical and Biomedical Analysis, 30, pp. 1451-1458.*
Chou et al. (Biochem. 1980, 19, 1543-1549).*
Durst et al. (Clinc. Chem. 1972, 18, 206-208).*
PCT/NO2005/000281 ISR & Written Opinion dated Nov. 2005.
Wolber, J. et.al., "Generating highly polarized nuclear spins in solution using dynamic nuclear polarization" Nuclear Instruments & Methods in Physics Research, Section A: Accelerators, Spectrometers, Detectors, and Associated Equipment, Coden: Nimaer; ISSN: 0168-9002, vol. 526, No. 1-2, Jun. 21, 2004, pp. 173-181.
Gould, Paula "C-13 MR Tracers Carbon-13 Nuclei Can Generate MR's High Contrast and Pet's High Specificity" Molecular Imaging Outlook, Diagnostic Imaging, Jun. 2004 Internet Citation XP002363324.

* cited by examiner

*Primary Examiner* — Michael G Hartley
*Assistant Examiner* — Melissa Perreira

(57) ABSTRACT

The invention relates to a method of producing a composition comprising hyperpolarised $^{13}$C-pyruvate, the composition and its use as an imaging agent for MR imaging.

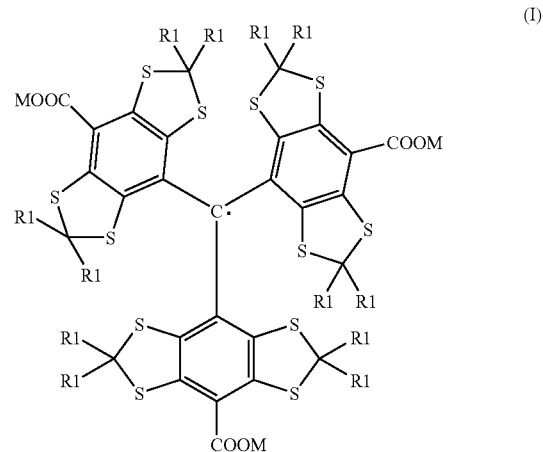

12 Claims, 2 Drawing Sheets

METHOD OF PRODUCING A COMPOSITION, COMPOSITION AND ITS USE

This application is a filing under 35 U.S.C. 371 of international application number PCT/NO2005/00281. filed Jul. 28, 2005, which claims priority to application number 20043229 filed Jul. 30, 2004, in Norway the entire disclosure of which is hereby incorporated by reference.

The invention relates to a method of producing a composition comprising hyperpolarised $^{13}$C-pyruvate, the composition and its use as an imaging agent for MR imaging.

Magnetic resonance (MR) imaging (MRI) is a imaging technique that has become particularly attractive to physicians as it allows for obtaining images of a patients body or parts thereof in a non-invasive way and without exposing the patient and the medical personnel to potentially harmful radiation such as X-ray. Because of its high quality images, MRI is the favourable imaging technique of soft tissue and organs and it allows for the discrimination between normal and diseased tissue, for instance tumours and lesions.

MR tumour imaging may be carried out with or without MR contrast agents. On an MR image taken without contrast agent, tumours from about 1-2 centimeters in size and larger will show up fairly clearly. However, contrast-enhanced MRI enables much smaller tissue changes, i.e. much smaller tumours to be detected which makes contrast-enhanced MR imaging a powerful tool for early stage tumour detection and detection of metastases.

Several types of contrast agents have been used in MR tumour imaging. Water-soluble paramagnetic metal chelates, for instance gadolinium chelates like Omniscan™ (Amersham Health) are widely used MR contrast agents. Because of their low molecular weight they rapidly distribute into the extracellular space (i.e. the blood and the interstitium) if administered into the vasculature. They are also cleared relatively rapidly from the body. Gadolinium chelates have been found to be especially useful in increasing the detection rate of metastases, small tumours, and improving tumour classification, the latter by allowing the differentiation of vital tumour tissue (well perfused and/or impaired blood-brain-barrier) from central necrosis and from surrounding oedema or macroscopically uninvolved tissue (see for instance C. Claussen et al., Neuroradiology 1985; 27: 164-171).

Blood pool MR contrast agents on the other hand, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours for example as a result of angiogenesis.

Despite the undisputed excellent properties of the aforementioned contrast agents their use is not without any risks. Although paramagnetic metal chelate complexes have usually high stability constants, it is possible that toxic metal ions are released in the body after administration. Further, these type of contrast agents show poor specificity.

WO-A-99/35508 discloses a method of MR investigation of a patient using a hyperpolarised solution of a high $T_1$ agent as MR imaging agent. The term "hyperpolarisation". means enhancing the nuclear polarisation of NMR active nuclei present in the high $T_1$ agent, i.e. nuclei with non-zero nuclear spin, preferably $^{13}$C- or $^{15}$N-nuclei. Upon enhancing the nuclear polarisation of NMR active nuclei, the population difference between excited and ground nuclear spin states of these nuclei are significantly increased and thereby the MR signal intensity is amplified by a factor of hundred and more. When using a hyperpolarised $^{13}$C and/or $^{15}$N-enriched high $T_1$ agent, there will be essentially no interference from background signals as the natural abundance of $^{13}$C and/or $^{15}$N is negligible and thus the image contrast will be advantageously high. A variety of possible high $T_1$ agents suitable for hyperpolarisation and subsequent use as MR imaging agents are disclosed including but not limited to non-endogenous and endogenous compounds like acetate, pyruvate, oxalate or gluconate, sugars like glucose or fructose, urea, amides, amino acids like glutamate, glycine, cysteine or aspartate, nucleotides, vitamins like ascorbic acid, penicillin derivates and sulfonamides. It is further stated that intermediates in normal metabolic cycles such as the citric acid cycle like fumaric acid and pyruvic acid are preferred imaging agents for the imaging of metabolic activity.

It has to be stressed that the signal of a hyperpolarised imaging agent decays due to relaxation and—upon administration to the patient's body—dilution. Hence the $T_1$ value of the imaging agents in biological fluids (e.g. blood) must be sufficiently long to enable the agent to be distributed to the target site in the patient's body in a highly hyperpolarised state. Apart from the imaging agent having a high $T_1$ value, it is extremely favourable to achieve a high polarisation level.

Several hyperpolarising techniques are disclosed in WO-A-99/35508 one of them is the dynamic nuclear polarisation (DNP) technique whereby polarisation of the sample is effected by a paramagnetic compound, the so-called paramagnetic agent or DNP agent. During the DNP process, energy, normally in the form of microwave radiation, is provided, which will initially excite the paramagnetic agent. Upon decay to the ground state, there is a transfer of polarisation from the unpaired electron of paramagnetic agent to the NMR active nuclei of the sample. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. The DNP technique is for example described in WO-A-98/58272 and in WO-A-01196895, both of which are included by reference herein.

The paramagnetic agent plays a decisive role in the DNP process and its choice has a major impact on the level of polarisation achieved. A variety of paramagnetic agents—in WO-A-99/35508 denoted as "OMRI contrast agents"—is known, for instance oxygen-based, sulfur-based or carbon-based organic free radicals or magnetic particles referred to in WO-A-99135508, WO-A-88/10419, WO-A-90/00904, WO-A-91/12024, WO-A-93/02711 or WO-A-96/39367.

BRIEF DESCRIPTION OF THE INVENTION

Figure 1:
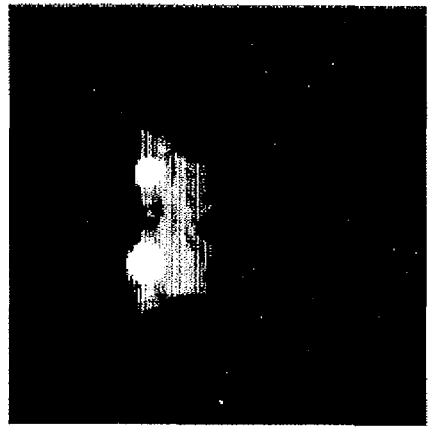
FIG. 1 displays a typical set of images of one imaged rat with (1) the proton reference image, wherein the arrows indicate the tumour locations, (2) the $^{13}$C-pyruvate image, (3) the $^{13}$C-lactate image (4) the $^{13}$C-alanine image (5) the $^{13}$C-lactate image corrected for $^{13}$C-pyruvate and (6) the $^{13}$C-lactate image corrected for $^{13}$C-alanine. Images (2) to (6) are fused with the proton reference image.
Figure 1:
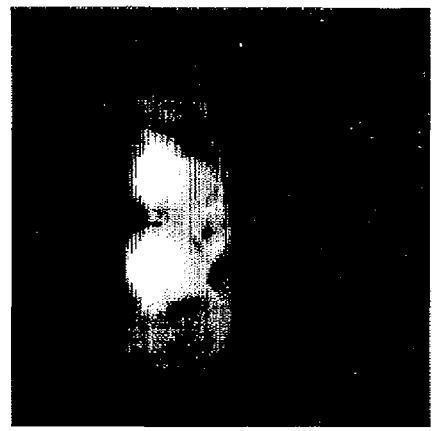
Figure 1:
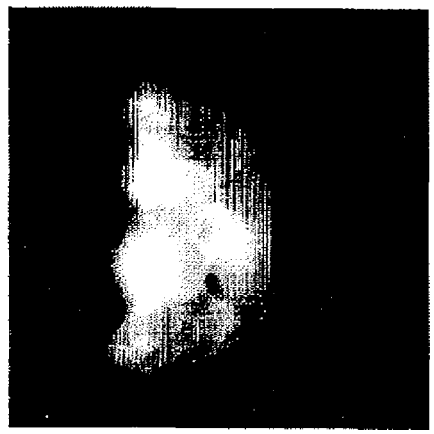
Figure 1:
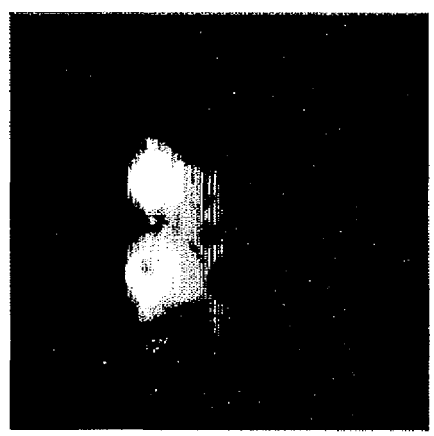
Figure 1:
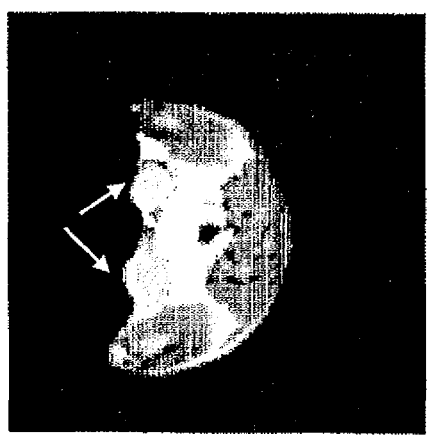
Figure 1:
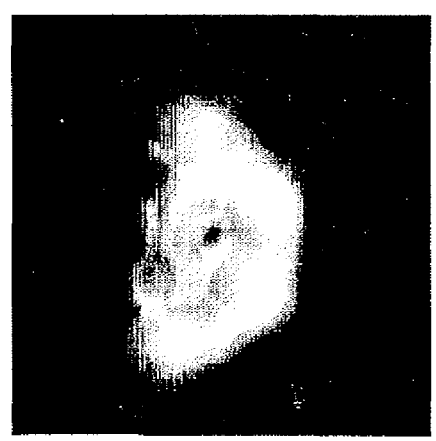

We have now surprisingly found an improved method for producing a liquid composition comprising hyperpolarised $^{13}$C-pyruvate which allows for obtaining hyperpolarised $^{13}$C- pyruvate with a remarkably high polarisation level. It has further been found that such a composition is especially suitable for in vivo MR tumour imaging.

Thus, viewed from one aspect, the present invention provides a method for producing a liquid composition comprising hyperpolarised $^{13}$C-pyruvate said method comprising a) forming a liquid mixture comprising a radical of formula (I), $^{13}$C-pyruvic acid and/or $^{13}$C-pyruvate and freezing the mixture;

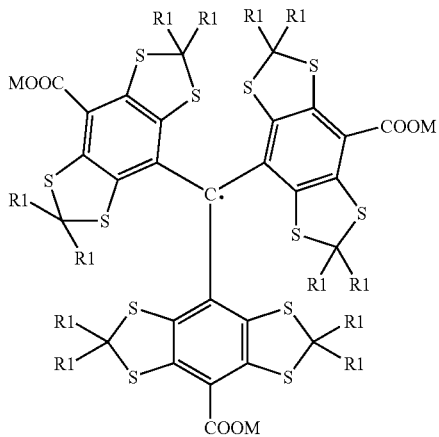

(I)

where

M represents hydrogen or one equivalent of a cation; and
R1 which is the same or different represents a straight chain or branched hydroxylated and/or alkoxylated $C_1$-$C_4$-hydrocarbon group b) enhancing the $^{13}$C nuclear polarisation of pyruvic acid and/or pyruvate in the mixture via DNP;
c) adding a buffer and a base to the frozen mixture to dissolve it and to convert the $^{13}$C-pyruvic acid into a $^{13}$C-pyruvate to obtain a liquid composition or, when only $^{13}$C-pyruvate is used in step a), adding a buffer to the frozen mixture to dissolve it to obtain a liquid composition; and
d) optionally removing the radical and/or reaction products thereof from the liquid composition The terms "hyperpolarised" and "polarised" are used interchangeably hereinafter and denote a polarisation to a level over that found at room temperature and 1 T.

A radical of formula (I) is used in the method of the invention

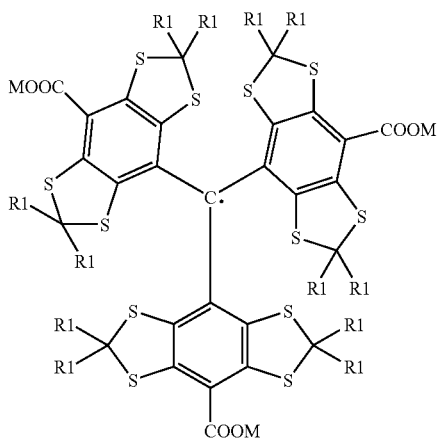

(I)

where

M represents hydrogen or one equivalent of a cation; and
R1 which is the same or different represents a straight chain or branched hydroxylated and/or alkoxylated $C_1$-$C_4$-hydrocarbon group.

Hereinafter, the term "radical" is used for the radical of formula (I).

In a preferred embodiment, M represents hydrogen or one equivalent of a physiologically tolerable cation. The term "physiologically tolerable cation" denotes a cation that is tolerated by the human or non-human animal living body. Preferably, M represents hydrogen or an alkali cation, an ammonium ion or an organic amine ion, for instance meglumine. Most preferably, M represents hydrogen or sodium.

In a further preferred embodiment, R1 is the same or different and represents hydroxymethyl or hydroxyethyl. In another preferred embodiment, R1 is the same or different and represents a straight chain or branched alkoxylated $C_1$-$C_4$-hydrocarbon group, preferably —$CH_2$—O—($C_1$-$C_3$-alkyl), —$(CH_2)_2$—O—$CH_3$ or —($C_1$-$C_3$-alkyl)-O—$CH_3$. In another preferred embodiment, R1 is the same or different and represents a straight chain or branched alkoxylated $C_1$-$C_4$-hydrocarbon group carrying a terminal hydroxyl group, preferably —$CH_2$—O—$C_2H_4OH$ or —$C_2H_4$—O—$CH_2OH$. In a more preferred embodiment, R1 is the same and represents a straight chain alkoxylated $C_1$-$C_4$-hydrocarbon group, preferably methoxy, —$CH_2$—$OCH_3$, $CH_2$—$OC_2Hs$ or $CH_2$—$CH_2$—$OCH_3$, most preferably —$CH_2$—$CH_2$—$OCH_3$.

In a most preferred embodiment, M represents hydrogen or sodium and R1 is the same and represents —$CH_2$—$CH_2$—$OCH_3$.

The synthesis of the radicals is known in the art and disclosed in WO-A-91/12024, WO-A-96/39367, WO 97/09633 and WO-A-98/39277. Briefly, the radicals may be synthesized by reacting three molar equivalents of a metallated monomeric aryl compound with one molar equivalent of a suitably protected carboxylic acid derivative to form a trimeric intermediate. This intermediate is metallated and subsequently reacted with e.g. carbon dioxide to result in a tricarboxylic trityl carbinol which, in a further step, is treated with a strong acid to generate a triarylmethyl cation. This cation is then reduced to form the stable trityl radical.

The isotopic enrichment of the $^{13}$C-pyruvic acid and/or $^{13}$C-pyruvate used in the method of the invention is preferably at least 75%, more preferably at least 80% and especially preferably at least 90%, an isotopic enrichment of over 90% being most preferred. Ideally, the enrichment is 100%. $^{13}$C-pyruvic acid and/or $^{13}$C-pyruvate may be isotopically enriched at the C1-position (in the following denoted $^{13}C_1$-pyruvic acid and $^{13}C_1$-pyruvate), at the C2-position (in the following denoted $^{13}C_2$-pyruvic acid and $^{13}C_2$-pyruvate), at the C3-position (in the following denoted $^{13}C_3$-pyruvic acid and $^{13}C_3$-pyruvate), at the C1- and the C2-position (in the following denoted $^{13}C_{1,2}$-pyruvic acid and $^{13}C_{1,2}$-pyruvate), at the C1- and the C3-position (in the following denoted $^{13}C_{1,3}$-pyruvic acid and $^{13}C_{1,3}$-pyruvate), at the C2- and the C3-position (in the following denoted $^{13}C_{2,3}$-pyruvic acid and $^{13}C_{2,3}$-pyruvate) or at the C1-, C2- and C3-position (in the following denoted $^{13}C_{1,2,3}$-pyruvic acid and $^{13}C_{1,2,3}$-pyruvate); the C1-position being the preferred one.

Several methods for the synthesis of $^{13}C_1$-pyruvic acid are known in the art. Briefly, Seebach et al., Journal of Organic Chemistry 40(2), 1975, 231-237 describe a synthetic route that relies on the protection and activation of a carbonyl-containing starting material as an S,S-acetal, e.g. 1,3-dithian or 2-methyl-1,3-dithian. The dithian is metallated and reacted with a methyl-containing compound and/or $^{13}CO_2$. By using the appropriate isotopically enriched $^{13}C$-component as outlined in this reference, it is possible to obtain $^{13}C_1$-pyruvate, $^{13}C_2$-pyruvate or $^{13}C_{1\text{-}2}$-pyruvate. The carbonyl function is subsequently liberated by use of conventional methods described in the literature. A different synthetic route starts from acetic acid, which is first converted into acetyl bromide and then reacted with $Cu^{13}CN$. The nitril obtained is converted into pyruvic acid via the amide (see for instance S. H. Anker et al., J. Biol. Chem. 176 (1948), 1333 or J. E. Thirkettle, Chem. Commun. (1997), 1025). Further, $^{13}C$-pyruvic acid may be obtained by protonating commercially available sodium $^{13}C$-pyruvate, e.g. by the method described in U.S. Pat. No. 6,232,497.

Whether $^{13}C$-pyruvic acid and/or $^{13}C$-pyruvate is used in the method of the invention is mainly dependent on the radical employed. If the radical is soluble in $^{13}C$-pyruvic acid, then $^{13}C$-pyruvic acid is preferably used and a liquid mixture, preferably a liquid solution is formed by the radical and $^{13}C$-pyruvic acid. If the radical is not soluble in $^{13}C$-pyruvic acid, then $^{13}C$-pyruvate and/or $^{13}C$-pyruvic acid and at least one co-solvent are used to form a liquid mixture, preferably a liquid solution. It has been found that the success of the polarisation in step b) and thus the level of polarisation is dependent on the compound to be polarised and the radical being in intimate contact with each other. Hence the co-solvent is preferably a co-solvent or co-solvent mixture that dissolves both, the radical and $^{13}C$-pyruvic acid and/or $^{13}C$-pyruvate. For $^{13}C$-pyruvate water is preferably used as a co-solvent.

Further, it has been found that higher polarisation levels in step b) are achieved when the mixture upon cooling/freezing forms a glass rather than a crystallized sample. Again, the formation of a glass allows a more intimate contact of the radical and the compound to be polarised. $^{13}C$-pyruvic acid is a good glass former and is therefore preferably used in the method of the invention, whenever the radical is soluble in $^{13}C$-pyruvic acid. $^{13}C$-pyruvate is a salt and a liquid mixture of an aqueous solution of $^{13}C$-pyruvate and a radical will result in a crystallized sample upon freezing. To prevent this, it is preferred to add further co-solvents which are good glass formers like glycerol, propanediol or glycol.

Hence in one embodiment, $^{13}C$-pyruvate is dissolved in water to obtain an aqueous solution and a radical, glycerol and optionally a further co-solvent are added to form a liquid mixture according to step a) of the method of the invention. In a preferred embodiment, $^{13}C$-pyruvic acid, a radical and a co-solvent are combined to form a liquid mixture according to step a) of the method of the invention. In a most preferred embodiment, $^{13}C$-pyruvic acid and a radical are combined to form a liquid mixture according to step a) of the method of the invention. Intimate mixing of the compounds can be achieved by several means known in the art, such as stirring, vortexing or sonification.

The liquid mixture of step a) according to the method of the invention preferably contains 5 to 100 mM radical, more preferably 10 to 20 mM radical, especially preferably 12 to 18 mM radical and most preferably 13 to 17 mM radical. It has been found that the build-up time for polarisation in step b) of the method of the invention is shorter using higher amounts of radical, however, the achievable polarisation level is lower. Hence these two effects have to be balanced against each other.

The liquid mixture in step a) of the method according to the invention is frozen before the polarisation of step b) is carried out. Cooling/freezing of the liquid mixture may be achieved by methods known in the art, e.g. by freezing the liquid mixture in liquid nitrogen or by simply placing it in the polarizer, where liquid helium will freeze the sample.

In step b) of the method according to the invention, the $^{13}C$ nuclear polarisation of $^{13}C$-pyruvic acid and/or $^{13}C$-pyruvate is enhanced via DNP. As described previously, dynamic nuclear polarisation (DNP) is a polarisation method where polarisation of the compound to be polarised is effected by a DNP agent, i.e. a paramagnetic compound. With respect to the method of the invention, polarisation is effected by the radical employed. During the DNP process, energy, preferably in the form of microwave radiation, is provided, which will initially excite the radical. Upon decay to the ground state, there is a transfer of polarisation from the unpaired electron of the radical to the $^{13}C$ nuclei of the $^{13}C$-pyruvic acid and/or $^{13}C$-pyruvate.

The DNP technique is for example described in WO-A-98/58272 and in WO-A-01/96895, both of which are included by reference herein. Generally, a moderate or high magnetic field and a very low temperature are used in the DNP process, e.g. by carrying out the DNP process in liquid helium and a magnetic field of about 1 T or above. Alternatively, a moderate magnetic field and any temperature at which sufficient polarisation enhancement is achieved may be employed. In a preferred embodiment of the method of the invention, the DNP process is carried out in liquid helium and a magnetic field of about 1 T or above. Suitable polarisation units for carrying out step b) of the method of the invention are for instance described in WO-A-02/37132. In a preferred embodiment, the polarisation unit comprises a cryostat and polarising means, e.g. a microwave chamber connected by a wave guide to a microwave source in a central bore surrounded by magnetic field producing means such as a superconducting magnet. The bore extends vertically down to at least the level of a region P near the superconducting magnet where the magnetic field strength is sufficiently high, e.g. between 1 and 25 T, for polarisation of the $^{13}C$ nuclei to take place. The sample bore is preferably sealable and can be evacuated to low pressures, e.g. pressures in the order of 1 mbar or less. A sample (i.e. the frozen mixture of step a) of the method of the invention) introducing means such as a removable sample-transporting tube can be contained inside the bore and this tube can be inserted from the top of the bore down to a position inside the microwave chamber in region P. Region P is cooled by liquid helium to a temperature low enough to for polarisation to take place, preferably temperatures of the order of 0.1 to 100 K, more preferably 0.5 to 10 K, most preferably 1 to 5 K. The sample introducing means is preferably sealable at its upper end in any suitable way to retain the partial vacuum in the bore. A sample-retaining container, such as a sample-retaining cup, can be removably fitted inside the lower end of the sample introducing means. The sample-retaining container is preferably made of a lightweight material with a low specific heat capacity and good cryogenic properties such, e.g. KelF (polychlorotrifluoroethylene) or PEEK (polyetheretherketone). The sample container may hold one or more samples to be polarised.

The sample is inserted into the sample-retaining container, submerged in the liquid helium and irradiated with microwaves, preferably at a frequency about 94 GHz at 200 mW. The level of polarisation may be monitored by acquiring solid state $^{13}C$-NMR signals of the sample during microwave irradiation, thus the use of a polarising unit containing means to acquire solid state $^{13}C$-NMR spectra in step b) is preferred. Generally, a saturation curve is obtained in a graph showing $^{13}C$-NMR signal vs. time. Hence it is possible to determine when the optimal polarisation level is reached.

In step c) of the method of the invention, the frozen polarised mixture is dissolved in a buffer, preferably a physiologically tolerable buffer, to obtain a liquid composition. The term "buffer" in the context of this application denotes one or more buffers, i.e. also mixtures of buffers.

Preferred buffers are physiologically tolerable buffers, more preferably buffers which buffer in the range of about pH 7 to 8 like for instance phosphate buffer ($KH_2PO_4$/$Na_2HPO_4$), ACES, PIPES, imidazole/HCl, BES, MOPS, HEPES, TES, TRIS, HEPPS or TRICIN. More preferred buffers are phosphate buffer and TRIS, most preferred is TRIS. In another embodiment, more than one of the aforementioned preferred buffers, i.e. a mixture of buffers, is used.

When $^{13}C$-pyruvic acid was used in the compound to be polarised, step c) also encompasses the conversion of $^{13}C$-pyruvic acid to $^{13}C$-pyruvate. To achieve this, $^{13}C$-pyruvic acid is reacted with a base. In one embodiment, $^{13}C$-pyruvic acid is reacted with a base to convert it to $^{13}C$-pyruvate and subsequently a buffer is added. In another preferred embodiment the buffer and the base are combined in one solution and this solution is added to $^{13}C$-pyruvic acid, dissolving it and converting it into $^{13}C$-pyruvate at the same time. In a preferred embodiment, the base is an aqueous solution of NaOH, $Na_2CO_3$ or $NaHCO_3$, most preferred the base is NaOH. In a particularly preferred embodiment, a solution of TRIS buffer containing NaOH is used to dissolve $^{13}C$-pyruvic acid and convert it into the sodium salt of $^{13}C$-pyruvate.

In another preferred embodiment, the buffer or—where applicable—the combined buffer/base solution further comprises one or more compounds which are able to bind or complex free paramagnetic ions, e.g. chelating agents like DTPA or EDTA. It has been found that free paramagnetic ions may cause shortening of the $T_1$ of the hyperpolarised compound, which is preferably avoided.

The dissolution may be carried out by preferably using the methods and/or devices disclosed in WO-A-02/37132. Briefly, a dissolution unit is used which is either physically separated from the polariser or is a part of an apparatus that contain the polariser and the dissolution unit. In a preferred embodiment, step c) is carried out at an elevated magnetic field to improve the relaxation and retain a maximum of the hyperpolarisation. Field nodes should be avoided and low field may lead to enhanced relaxation despite the above measures.

In the optional step d) of the method of the invention, the radical and/or reaction products thereof are removed from the liquid composition obtained in step c). The radical and/or reaction products may be removed partially, substantially or ideally completely, the complete removal is preferred when the liquid composition is used in a human patient. Reaction products of the radical might be esters which may be formed upon reaction of pyruvic acid with radicals of formula (I) comprising hydroxy groups. In a preferred embodiment of the method of the invention, step d) is mandatory. Methods usable to remove the radical and/or reaction products thereof are known in the art. Generally, the methods applicable depend on the nature of the radical and/or its reaction products. Upon dissolution of the frozen mixture in step c), the radical might precipitate and it may easily be separated from the liquid composition by filtration. If no precipitation occurs, the radical may be removed by chromatographic separation techniques, e.g. liquid phase chromatography like reversed phase or ion exchange chromatography or by extraction.

As radicals of formula (I) have a characteristic UV/visible absorption spectrum, it is possible to use UV/visible absorption measurement as a method to check for its existence in the liquid composition after its removal. In order to obtain quantitative results, i.e. the concentration of the radical present in the liquid composition, the optical spectrometer can be calibrated such that absorption at a specific wavelength form a sample of the liquid composition yields the corresponding radical concentration in the sample. Removal of the radical and/or reaction products thereof is especially preferred if the liquid composition is used as an imaging agent for in vivo MR imaging of a human or non-human animal body.

From a further aspect, the present invention provides a composition comprising hyperpolarised $^{13}C$-pyruvate, preferably hyperpolarised sodium $^{13}C$-pyruvate and a buffer selected from the group consisting of phosphate buffer and TRIS.

In a preferred embodiment, the hyperpolarised $^{13}C$-pyruvate has a polarisation level of at least 10%, more preferably at least 15%, particularly preferably at least 20% and most preferably more than 20%.

It has been found that such compositions are excellent imaging agents for in vivo MR imaging, especially for in vivo MR studying of metabolic processes and for in vivo MR tumour imaging and a composition comprising hyperpolarised $^{13}C$-pyruvate and a buffer selected from the group consisting of phosphate buffer and TRIS for use as a MR imaging agent forms another aspect of the invention.

The composition of the invention is preferably produced by the method as claimed in claim 1, more preferably by using $^{13}C$-pyruvate in step a) of the method of claim 1 and a radical of formula (I) where M is hydrogen or a physiologically tolerable cation and R1 is the same and represents a straight chain or branched alkoxylated $C_1$-$C_4$-hydrocarbon group, preferably methoxy, —$CH_2$—$OCH_3$, —$CH_2$—$OC_2H_5$ or —$CH_2$—$CH_2$—$OCH_3$ and step d) is mandatory. In a particularly preferred embodiment, the composition of the invention is produced by the method as claimed in claim 1 wherein in step a) $^{13}C$-pyruvate and a radical of formula (I) where M represents hydrogen and R1 is the same and represents $CH_2$—$CH_2$—$OCH_3$ are used and step d) is mandatory.

Another aspect of the invention is the use of a composition comprising hyperpolarised $^{13}C$-pyruvate, preferably hyperpolarised sodium $^{13}C$-pyruvate and a buffer selected from the group consisting of phosphate buffer and TRIS for the manufacture of a MR imaging agent for in vivo studying of metabolic processes in the human or non-human animal body.

Yet another aspect of the invention is the use of a composition comprising hyperpolarised $^{13}C$-pyruvate, preferably hyperpolarised sodium $^{13}C$-pyruvate and a buffer selected from the group consisting of phosphate buffer and TRIS for the manufacture of a MR imaging agent for in vivo tumour imaging in the human or non-human animal body, preferably for in vivo tumour diagnosis and/or tumour staging and/or tumour therapy monitoring, more preferably for in vivo prostate tumour diagnosis and/or prostate tumour staging and/or prostate tumour therapy monitoring.

The composition according to the invention may be used as a "conventional" MR imaging agent, i.e. providing contrast enhancement for anatomical imaging. A further advantage of the composition according to the invention is, that pyruvate is an endogenous compound which is very well tolerated by the human body, even in high concentrations. As a precursor in the citric acid cycle, pyruvate plays an important metabolic role in the human body. Pyruvate is converted into different compounds: its transamination results in alanine, via oxidative decarboxylation, pyruvate is converted into acetyl-CoA and bicarbonate, the reduction of pyruvate results in lactate and its carboxylation in oxaloacetate.

It has now been found that the conversion of hyperpolarised $^{13}C$-pyruvate to hyperpolarised $^{13}C$-lactate, hyperpolarised $^{13}C$-bicarbonate (in the case of $^{13}C_1$-pyruvate, $^{13}C_{1,2}$-pyruvate or $^{13}C_{1,2,3}$-pyruvate only) and hyperpolarised $^{13}C$-alanine can be used for in vivo MR studying of metabolic processes in the human body. This is surprising as one has to bear in mind that the $T_1$ of hyperpolarised compounds decays due to relaxation and dilution. $^{13}C$-pyruvate has a $T_1$ relaxation in human full blood at 37° C. of about 42 s, however, the conversion of hyperpolarised $^{13}C$-pyruvate to hyperpolarised $^{13}C$-lactate, hyperpolarised $^{13}C$-bicarbonate and hyperpolarised $^{13}C$-alanine has been found to be fast enough to allow signal detection from the $^{13}C$-pyruvate parent compound and its metabolites. The amount of alanine, bicarbonate and lactate is dependent on the metabolic status of the tissue under investigation. The MR signal intensity of hyperpolarised $^{13}C$-lactate, hyperpolarised $^{13}C$-bicarbonate and hyperpolarised $^{13}C$-alanine is related to the amount of these compounds and the degree of polarisation left at the time of detection, hence by monitoring the conversion of hyperpolarised $^{13}C$-pyruvate to hyperpolarised $^{13}C$-lactate, hyperpolarised $^{13}C$-bicarbonate and hyperpolarised $^{13}C$-alanine it is possible to study metabolic processes in vivo in the human or non-human animal body by using non-invasive MR imaging.

It has been found that the MR signal amplitudes arising from the different pyruvate metabolites vary depending on the tissue type. The unique metabolic peak pattern formed by alanine, lactate, bicarbonate and pyruvate can be used as fingerprint for the metabolic state of the tissue under examination and thus allows for the discrimination between healthy tissue and tumour tissue. This makes the composition according to the invention an excellent agent for in vivo MR tumour imaging.

Generally, in order to carry out MR imaging with the composition according to the invention, the subject under examination, e.g. patient or an animal, is positioned in the MR magnet. Dedicated $^{13}C$-MR RF-coils are positioned to cover the area of interest.

The composition according to the invention, i.e. the composition comprising hyperpolarised $^{13}C$-pyruvate and a buffer selected from the group consisting of phosphate buffer and TRIS is administered parenterally, preferably intravenously, intraarterially or directly into the region or organ of interest. Dosage and concentration of the composition according to the invention will depend upon a range of factors such as toxicity, the organ targeting ability and the administration route. Generally the composition is administered in a concentration of up to 1 mmol pyruvate per kg bodyweight, preferably 0.01 to 0.5 mmol/kg, more preferably 0.1 to 0.3 mmol/kg. The administration rate is preferably less than 10 ml/s, more preferably less than 6 ml/min and most preferable of from 5 ml/s to 0.1 ml/s. At less than 400 s after the administration, preferably less than 120 s, more preferably less than 60 s after the administration, especially preferably 20 to 50 s after the administration and most preferably 30 to 40 s after the administration, an MR imaging sequence is applied that encodes the volume of interest in a combined frequency and spatial selective way. This will result in metabolic images of $^{13}C$-lactate, $^{13}C$-alanine and $^{13}C$-pyruvate and more preferably in metabolic images of $^{13}C$-lactate, $^{13}C$-alanine, $^{13}C$-bicarbonate and $^{13}C$-pyruvate. Within the same period of time, a proton image with or without a proton MRI contrast agent may be acquired to obtain anatomical and/or perfusion information.

The encoding of the volume of interest can be achieved by using so-called spectroscopic imaging sequences as described in for instance T. R. Brown et al., Proc. Natl. Acad. Sci. USA 79, 3523-3526 (1982); A. A. Maudsley, et al. J. Magn. Res 51, 147-152 (1983). Spectroscopic image data contain a number of volume elements in which each element contains a full $^{13}C$-MR spectrum. $^{13}C$-pyruvate and its $^{13}C$-metabolites all have their unique position in a $^{13}C$-MR spectrum and their resonance frequency can be used to identify them. The integral of the peak at its resonance frequency is directly linked to the amount of $^{13}C$-pyruvate and its $^{13}C$-metabolites, respectively. When the amount of $^{13}C$-pyruvate and each $^{13}C$-metabolite is estimated using time domain fitting routines as described for instance in L. Vanhamme et al., J Magn Reson 129, 3543 (1997), images can be generated for $^{13}C$-pyruvate and each $^{13}C$-metabolite in which a colour coding or grey coding is representative for the amount of $^{13}C$-pyruvate and each $^{13}C$-metabolite measured.

Although spectroscopic imaging methods have proven their value in producing metabolic images using all kind of MR nuclei e.g. $^1H$, $^{31}P$, $^{23}Na$, the amount of repetitions needed to fully encode the spectroscopic image makes this approach less suitable for hyperpolarized $^{13}C$. Care has to be taken to ensure hyperpolarized $^{13}C$-signal is available during the whole MR data acquisition. At the expense of a reduced signal to noise, this can be achieved by reducing the RF-pulse angle that is applied in every phase encoding step. Higher matrix sizes require more phase encoding steps and longer scan times.

Imaging methods based on the pioneering work by P. C. Lauterbur (Nature, 242, 190-191, (1973) and P. Mansfield (J. Phys. C. 6, L422-L426 (1973)), implying applying a readout gradient during the data acquisition, will allow for higher signal to noise images or the equivalent, higher spatial resolution images. However, these imaging methods in their basic form will not be able to produce separate images for $^{13}C$-pyruvate and its $^{13}C$-metabolites but an image containing the signals of $^{13}C$-pyruvate and all of its $^{13}C$-metabolites, i.e. the identification of specific metabolites is not possible.

In a preferred embodiment, imaging sequences are used that will make use of multi-echoes to code for the frequency information. Sequences that can produce separate water and fat $^1H$-images are for example described in G. Glover, J Magn Reson Imaging 1991; 1:521-530 and S. B. Reeder et al., MRM 51 35-45 (2004). Since the metabolites to be detected and as such their MR frequencies are known, the approach discussed in the references above can be applied to directly image pyruvate, alanine and lactate and preferably pyruvate, alanine, lactate and bicarbonate and makes more efficient use of the hyperpolarised $^{13}C$-MR signal, giving a better signal quality compared to the classical spectroscopic imaging technique, a higher spatial resolution and faster acquisition times.

Tumour tissue is often characterised by an increased perfusion and higher metabolic activity. The process of increasing the vascular bed, angiogenesis, is induced by cells that due to their higher metabolic needs and/or their larger distance from a capillary are not able to get enough substrates that can provide the energy needed to sustain energy homeostasis. It is in this area, where cells have problems in producing enough energy, a marked change in metabolic pattern is expected. Tissue with problems sustaining energy homeostasis will alter its energy metabolism which in particular results in an increased lactate production. Surprisingly, it is possible to make this change in metabolism visible using hyperpolarised $^{13}C$-pyruvate within the short MR imaging time window available, i.e. using the high $^{13}C$-lactate signal in the tumour area to discriminate the tumour from healthy tissue. As the perfusion is heterogeneous in tumour tissue, it is preferred to correct the $^{13}C$-lactate signal for the amount of pyruvate ($^{13}C$-pyruvate signal) available in the same region. This will allow for emphasising regions in the tissue with a relative high lactate signal with respect to the pyruvate signal and thus improve the discrimination between tumour tissue and healthy tissue.

To correct for the pyruvate signal, both lactate and pyruvate images are normalized to the maximum value in each individual image. Second, the normalized lactate image is multiplied by the inverted pyruvate image, e.g. the maximum pyruvate signal in the image minus the pyruvate level for every pixel. As a last step, the intermediate result gained in the operation above is multiplied by the original lactate image.

To emphasise regions with altered metabolism, the high $^{13}$C-lactate signal in connection with a reduced $^{13}$C-alanine signal can be used in a similar operation as described in the paragraph above. Surprisingly, the identification of the tumour area, i.e. the discrimination between tumour tissue and healthy tissue is improved by this correction as well. To correct for the alanine signal, both lactate and alanine images are normalized to the maximum value in each individual image. Second, the normalized lactate image is multiplied by the inverted alanine image, e.g. the maximum alanine signal in the image minus the alanine level for every pixel. As a last step, the intermediate result gained in the operation above is multiplied by the original lactate image. In a similar manner, the $^{13}$C-bicarbonate signal may be included in the analysis as well. Further a proton image acquired with our without a proton MRI contrast agent may be included in the analysis to obtain anatomical and/or perfusion information.

In another preferred embodiment, the composition according to the invention is administered repeatedly, thus allowing dynamic studies. This is a further advantage of the composition in comparison to other MR imaging agents which, due to their relatively long circulation in the patient's body, do not allow such dynamic studies.

The composition according to the invention is further useful as an imaging agent for in vivo MR tumour staging. The same metabolic images and/or metabolic ratio images as described in the preceding paragraphs may be used for this purpose with appropriate cut off categories defined dependent on tumour size and metabolic activity.

Further, the composition according to the invention is useful as an imaging agent for in vivo MR tumour therapy monitoring, e.g. by monitoring direct changes in metabolism pattern of tumours upon treatment with therapeutic antitumour agents and/or radiation treatment or in connection with any type of interventional techniques with or without any kind of ablation, i.e. chemical ablation combined with radio frequencies, microwaves or ultrasound.

Tumour MR imaging can be influenced and improved by preparing the patient or the animal in a way that will perturb the protein metabolism, lipid metabolism or energy metabolism in general. Ways to achieve this are known in the art, e.g. by abrosia (for instance over night), glucose infusion and the like.

In a preferred embodiment, the composition according to the invention is useful as an imaging agent for in vivo MR tumour imaging, tumour therapy monitoring and tumour staging of brain tumours, breast tumours, colon/colo-rectal tumours, lung tumours, kidney tumours, head and neck tumours, muscle tumours, gastric tumours, esophageal tumours, ovarian tumours, pancreas tumours and prostate tumours. It has further been found that the composition according to the invention is especially useful as an imaging agent for in vivo MR prostate tumour imaging, i.e. prostate tumour diagnosis and/or prostate tumour staging and/or prostate tumour therapy monitoring.

When a man presents to the doctor with symptoms of urinary pain or discomfort, prostate cancer is suspected. If the man is over 50 years, a Prostate Specific Antigen (PSA) test is performed. Prostate cancer is suspected on the basis of an elevated PSA and/or abnormal Digital Rectal Examination (DRE). If the PSA test is positive, the patient is sent to a specialist (an urologist) for diagnosis using ultrasound guided biopsy. Of the two million biopsy procedures per year performed in the US and Europe, 5 out of 6 and 2 out of 3 are negative, respectively. When detected at an early stage, the five-year survival rate for these patients is 100%. As prostate cancer is the most common cancer and the second leading cause of cancer death in men, there is a strong medical demand for a method for the diagnosis of prostate tumours which is capable of detecting prostate tumours at an early stage and which could help to reduce the number of biopsy procedures.

The $^{13}$C-imaging of the prostate requires a transmit-receive volume $^{13}$C-RF-coil, preferably, a transmit volume $^{13}$C-RF-coil in combination with a MR receive only endorectal RF-coil is used and more preferably, a transmit-receive phased array volume $^{13}$C-RF-coil in combination with a MR receive only endorectal $^{13}$C-RF-coil is used. Especially preferred are coils that make the acquisition of a $^{1}$H-prostate image possible after the $^{13}$C-imaging.

Another aspect of the invention is a composition comprising $^{13}$C-pyruvic acid and/or $^{13}$C-pyruvate and the radical of formula (I).

In a preferred embodiment, said composition comprises a radical of formula (I) where M represents hydrogen or one equivalent of a physiologically tolerable cation. Preferably, M represents hydrogen or an alkali cation, an ammonium ion or an organic amine ion, for instance meglumine. Most preferably, M represents hydrogen or sodium.

In a further preferred embodiment, said composition comprises a radical of formula (I) where R1 is the same or different and represents hydroxymethyl or hydroxyethyl. In another preferred embodiment, R1 is the same or different and represents a straight chain or branched alkoxylated $C_1$-$C_4$-hydrocarbon group, preferably —$CH_2$—O—($C_1$-$C_3$-alkyl), —$(CH_2)_2$—O—$CH_3$ or —($C_1$-$C_3$-alkyl)-O—$CH_3$. In another preferred embodiment, R1 is the same or different and represents a straight chain or branched alkoxylated $C_1$-$C_4$-hydrocarbon group carrying a terminal hydroxyl group, preferably —$CH_2$—O—$C_2H_4OH$ or —$C_2H_4$—O—$CH_2OH$. In a more preferred embodiment, R1 is the same and represents a straight chain alkoxylated $C_1$-$C_4$-hydrocarbon group, preferably methoxy, —$CH_2$—$OCH_3$, —$CH_2$—$OC_2H_5$ or —$CH_2$—$CH_2$—$OCH_3$, most preferably —$CH_2$—$CH_2$—$OCH_3$.

In a particularly preferred embodiment, said composition comprises a radical of formula (I) where M represents hydrogen or sodium and R1 is the same and represents —$CH_2$—$CH_2$—$OCH_3$.

In a further preferred embodiment, said composition comprises $^{13}$C-pyruvic acid and/or $^{13}$C-pyruvate with an isotopic enrichment of at least 75%, more preferably at least 80% and especially preferably at least 90%, an isotopic enrichment of over 90% being most preferred. Ideally, the enrichment is 100%. $^{13}$C-pyruvic acid and/or $^{13}$C-pyruvate may be isotopically enriched at the C1-position, at the C2-position, at the C3-position, at the C1- and C2-position, at the C1- and C3-position, at the C2- and C3-position or at the C1-, the C2- and the C3-position, with the C1-position being the preferred one.

In a particularly preferred embodiment, said composition comprises $^{13}$C-pyruvic acid and the radical of formula (I) where M represents hydrogen or sodium and R1 is the same and represents $CH_2$—$CH_2$—$OCH_3$, most preferably said composition contains $^{13}$C-pyruvic acid and the radical of formula (I) where M represents hydrogen or sodium and R1 is the same and represents —$CH_2$—$CH_2$—$OCH_3$.

The compositions according to the invention comprising $^{13}$C-pyruvic acid and/or $^{13}$C-pyruvate and the radical of formula (I) are particularly useful for the production of hyperpolarised $^{13}$C-pyruvate, for instance for the production of hyperpolarised $^{13}$C-pyruvate according to the method of the invention. Hence another aspect of the invention is the use of a composition comprising $^{13}$C-pyruvic acid and/or $^{13}$C-pyruvate and the radical of formula (I) for the production of hyperpolarised $^{13}$C-pyruvate.

The radicals of formula (I) where M represents hydrogen or sodium and R1 is the same and represents —$CH_2$—$CH_2$—$OCH_3$ were found to be particularly favourable for use in the method according to the invention due to the following properties: they are soluble in $^{13}$C-pyruvic acid and stable when dissolved therein. They further show high polarisation efficiency in step b) of the method according to the invention and are stable during the dissolution step c), also when a base is used in this step. They can easily be removed in step d) of the method of the invention by for instance filtration using a hydrophobic filter material.

Those radicals are new, hence another aspect of the invention are radicals of formula (I) where M represents hydrogen or sodium and R1 is the same and represents —$CH_2$—$CH_2$—$OCH_3$.

The radicals of the invention may be synthesized as described in Example 1. Briefly, the radicals may be synthesized by reacting three molar equivalents of a metallated monomeric aryl compound with one molar equivalent of a suitably protected carboxylic acid derivative to form a trimeric intermediate. This intermediate is metallated and subsequently reacted with e.g. carbon dioxide to result in a tricarboxylic trityl carbinol which, in a further step, is treated with a strong acid to generate a triarylmethyl cation. This cation is then reduced to form the stable trityl radical.

Yet a further aspect of the invention is the use of the radicals according to the invention as a paramagnetic agent for the hyperpolarisation of compounds in a DNP process.

EXAMPLES

Example 1

Synthesis of Tris(8-carboxy-2,2,6,6-(tetra(methoxyethyl)benzo-[1,2-4,5']bis-(1,3)dithiole-4-yl)methyl sodium salt 10 g (70 mmol) Tris(8-carboxy-2,2,6,6-(tetra(hydroxyethyl)benzo-[1,2-4,5']-bis-(1,3)-dithiole-4-yl)methyl sodium salt which had been synthesized according to Example 7 of WO-A1-98/39277 were suspended in 280 ml dimethylacetamide under an argon atmosphere. Sodium hydride (2.75 g) followed by methyl iodide (5.2 ml) was added and the reaction which is slightly exothermic was allowed to proceed for 1 hour in a 34° C. water bath for 60 min. The addition of sodium hydride and methyl iodide was repeated twice with the same amounts of each of the compounds and after the final addition, the mixture was stirred at room temperature for 68 hours and then poured into 500 ml water. The pH was adjusted to pH>13 using 40 ml of 1 M NaOH (aq) and the mixture was stirred at ambient temperature for 15 hours to hydrolyse the formed methyl esters. The mixture was then acidified using 50 ml 2 M HCl (aq) to a pH of about 2 and 3 times extracted the ethyl acetate (500 ml and 2×200 ml). The combined organic phase was dried over $Na_2SO_4$ and then evaporated to dryness. The crude product (24 g) was purified by preparative HPLC using acetonitrile/water as eluents. The collected fractions were evaporated to remove acetonitrile. The remaining water phase was extracted with ethyl acetate and the organic phase was dried over $Na_2SO_4$ and then evaporated to dryness. Water (200 ml) was added to the residue and the pH was carefully adjusted with 0.1 M NaOH (aq) to 7, the residue slowly dissolving during this process. After neutralization, the aqueous solution was freeze dried.

Example 2

Production of hyperpolarised $^{13}$C-pyruvate using $^{13}$C-pyruvic acid and the radical of Example 1

A 20 mM solution was prepared by dissolving 5.0 mg of the radical of Example 1 in $^{13}$C$_1$-pyruvic acid (164 μl). The sample was mixed to homogeneity and an aliquot of the solution (41 mg) was placed in a sample cup and inserted in the DNP polariser.

The sample was polarised under DNP conditions at. 1.2 K in a 3.35 T magnetic field under irradiation with microwave (93.950 GHz). After 2 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarized sodium $^{13}$C$_1$-pyruvate. The dissolved sample was rapidly analysed with $^{13}$C-NMR to assess the polarisation and a 19.0% $^{13}$C polarisation was obtained.

Example 3

Production of hyperpolarised $^{13}$C-pyruvate using $^{13}$C-pyruvic acid and the radical of Example 1

A 15 mM solution was prepared by dissolving the radical of Example 1 (209.1 mg) in a mixture of $^{13}$C$_1$-pyruvic acid (553 mg) and unlabelled pyruvic acid (10.505 g). The sample was mixed to homogeneity and an aliquot of the solution (2.015 g) was placed in a sample cup and inserted in the DNP polariser.

The sample was polarised under DNP conditions at 1.2 K in a 3.35 T magnetic field under irradiation with microwave (93.950 GHz). After 4 hours the polarisation was stopped and the sample was dissolved using a dissolution device according to WO-A-02/37132 in an aqueous solution of sodium hydroxide and tris(hydroxymethyl)aminomethane (TRIS) to provide a neutral solution of hyperpolarized sodium $^{13}$C$_1$-pyruvate with a total pyruvate concentration of 0.5 M in 100 mM TRIS buffer. In series with the dissolution device a chromatographic column was connected. The column consists of a cartridge (D=38 mm; h=10 mm) containing hydrophobic packing material (Bondesil-C18, 40 UM Part #:12213012) supplied by Varian. The dissolved sample was forced through the column which selectively adsorbed the radical. The filtered solution was rapidly analysed with $^{13}$C-NMR to assess the polarisation, 16.5% $^{13}$C polarisation was obtained. The residual radical concentration was subsequently analysed with a UV spectrophotometer at 469 nm and was determined to be below the detection limit of 0.1 μM.

Example 4

Production of hyperpolarised $^{13}C$-pyruvate using $^{13}C$-pyruvic acid and Tris(8-carboxy-2,2,6,6-tetra (hydroxyethoxy)methyl-benzo[1,2-d:4,5-d']bis(1,3) dithiole-4-yl)methyl sodium salt Tris(8-carboxy-2,2,6,6-tetra(hydroxyethoxy)methyl-benzo[1,2-d:4,5-d']-bis-(1,3)dithiole-4-yl)methyl sodium salt was synthesised as described in Example 29 in WO-A-97/09633.

A 20 mM solution was prepared by dissolving Tris(8-carboxy-2,2,6,6-tetra(hydroxyethoxy)methyl-benzo[1,2-d:4,5-d']-bis-(1,3)-dithiole-4-yl)methyl sodium salt in $^{13}C_1$-pyruvic acid (83.1 mg). The sample was mixed to homogeneity, placed in a sample cup and inserted in the DNP polariser. The sample was polarised under DNP conditions at 1.2 K in a 3.35 T magnetic field under irradiation with microwave (93.950 GHz). The $^{13}C$-NMR signal from the sample was acquired using a Varian Inova-200 NMR spectrometer. The DNP enhancement was calculated from a measurement of the thermal equilibrium $^{13}C$-NMR signal and the enhanced NMR signal. 16% $^{13}C$ polarisation was obtained.

Example 5

Tumour imaging using hyperpolarised $^{13}C$-pyruvate as imaging agent 5.1 Tumour Animal Model and Tumour Preparation R3230AC is a rat mammary adenocarcinoma that can be maintained in female Fischer 344 rats. To establish the animal tumour model, a frozen vial of R32030 cells containing RPMI 1640, 10% FBS and 10% DMSO was rapidly thawed in 37° C. Thereafter, the cell solution was transferred to FBS and increasing volumes of RPMI 1640 were added. Finally, the cell suspension was transferred to a 25 cm² growth flask and put into an incubator at 37° C., 5% $CO_2$. Growth media were changed every other day. At the day of rat infection, removal of cells was carried out either by mechanical force or by means of trypsin. Cells were washed using phosphate buffer lacking calcium and magnesium. Trypsin (0.05% trypsin in 0.02% EDTA) was added for 2-5 min. Then, 5 ml FBS was added and the cells were transferred into a beaker containing RPMI 1640 with FCS and antibiotics (100 IU/ml penicillin, 100 IU/ml streptomycin and 2.5 pg/ml amphotericin 6). The cell solution was centrifugated and the cell pellet was resuspended in 20 ml RPMI with FBS and antibiotics, centrifugation and resuspension was repeated. The cells were then aliquoted to vials containing $4 \times 10^6$ cells/ml RPMI 1640. To obtain donor tumours, female Fischer 344 rats (Charles River, 180-200 g) were anaesthetised and 0.3 ml of the cell suspension was subcutaneously injected in the inguinal region on both sides. 15 and 22 days later, pieces of tumour were prepared as described in F. A. Burgener et al., Invest Radiol 2216 (1987), 472-478; S. Saini et al., J. Magn. Reson, 129/1 (1997), 35-43). Two incisions were made on the ventral abdomen of recipient female Fischer rats. A tumour piece was inserted into each pocket and the incisions were closed. Rats were brought to imaging 12-14 days after tumour engrafting.

5.2 Rat Preparation and Proton MR Imaging

Weighed rats were anaesthetised using isoflurane (2-3%) and kept on a heated table to ensure a body temperature of about 37° C. A catheter was introduced into the tail vein and into the arteria carotis communis sinistra. The rats were transported to the MR machine and placed on a home-built pad that was heated to approx. 37° C. by means of circulating FC-104 Fluorinert. This liquid will not give rise to background signals in $^1H$- and $^{13}C$-MR imaging. Anaesthesia was continued by means of 1-2% isoflurane delivered via a long tube to an open-breathing system at a rate of 0.4 L/min. The arterial catheter was connected via a T-tube to a pressure recorder and a pump delivering saline (rate 0.15 L/min) to prevent catheter clotting. Rats were positioned in a rat MR coil (Rapid Biomedical, Germany) and imaging using a standard proton MR imaging sequence to get anatomical information and to determine the location of the tumour.

5.3 $^{13}C$-MR Imaging

Based on the proton frequency found by the MR system the MR frequency for $^{13}C_1$-alanine was calculated according to the following equation:

Frequency $^{13}C_1$-alanine=0.25144×[(system frequency proton×1.00021)−0.000397708]

The frequency calculated positioned the MR signal arising from $^{13}C_1$-alanine on resonance with $^{13}C_1$-lactate on the left and $^{13}C1$-pyruvate resonating on the right of $^{13}C_1$-alanine. An unlocalised MR spectroscopy sequence was run to ensure that the $^{13}C$-MR coil and the system MR frequency had been set up correctly. The $^{13}C$-image location was positioned to cover the tumour (slice thickness 10 mm, in plane pixel size 5×5 mm²). In the reconstruction phase, the image data was zero-filled to result in 2.5×2.5×10 mm³ resolution. $^{13}C_1$-pyruvate in TRIS buffer (90 mM) was injected in a dose of 10 ml/kg during a period of 12 s with a minimum volume of 2 ml into the tail vein and 30 s after the start of the injection (i.e. 18 s after finishing the injection), the chemical shift $^{13}C$-MR sequence was started.

5.4 Analysis of the MR Imaging Data

MR imaging resulted in a matrix containing 16×16 elements in which each element or voxel/pixel contains a $^{13}C$-MR spectrum. In the reconstruction phase, the matrix was zero-filled to 32×32, a mathematical operation that helps to improve the spatial resolution. The dataset to be analysed contained 1024 spectra as was exported to Dicom® format (DICOM is the registered trademark of the National Electrical Manufacturers Association for its standards publications relating to digital communications of medical information) for further analysis. About half of these spectra did not contain MR signals as the position of these voxels was outside the animal. A location within the animal revealed voxels with high pyruvate signals and negligible lactate and alanine signal (blood pool) while other voxels showed pyruvate, alanine and lactate in about equal intensity.

The amplitudes for pyruvate, alanine and lactate were estimated using time domain fitting procedures which included the following: the zero order phase is constant over the dataset, the first order phase is 1.4 ms, the line width or damping in the time domain is allowed to vary between 0.5 and 3 times the average line width of the whole dataset for each metabolite independently and the frequency is allowed to vary with 20 Hz in both directions with respect to the average frequency found over the whole dataset for the highest peak, which has to be identified by the user.

The amplitudes for lactate, alanine and pyruvate were reordered in a matrix and resampled to match the resolution of the proton anatomical MR image. The $^{13}C$-MR images were projected on the anatomical images using an automated procedure to obtain an operator-independent result. The results were displayed in image sets containing the anatomical proton image of the tumour in the rat, the metabolic $^{13}C$-image for pyruvate, lactate and alanine projected onto the anatomical image, images showing for every pixel a) $([\text{lactate}]_{norm} \times ([\text{pyruvate}]_{max} - [\text{pyruvate}])_{norm}) \times [\text{lactate}]$ and b) ([lactate]$_{norm}$×([alanine]$_{max}$−[alanine])$_{norm}$)×[lactate]
in which the term "[ . . . ]norm represents the normalised amplitude, i.e. scaled to its highest value in the metabolic image and [lactate] the amplitude calculated.

A successful result for the discrimination of tumour tissue and healthy tissue in a metabolic $^{13}$C-MR image was defined as highest lactate signal in the tumour area or a high weighted ratio lactate over pyruvate in the tumour area and a high weighted lactate over alanine ratio in the same pixel location.

5.5 Biological Analysis

Tumour sites were visually inspected to detect signs of bleeding. Tumours were liberated from the rat bodies, weighed and cut in half. Tumour interiors were inspected visually assessing homogeneity, necrosis and bleeding. The tumour tissues were stored in 4% formalin.

A tumour-bearing rat was considered to be appropriate for evaluation if the following criteria were met: tumour weight>100 mg, no visible necrosis or cysts in the tumour interior, a body temperature above 35° C. and a mean arterial blood pressure above 60 mm Hg at time of MR investigation.

5.6 Results

In total 30 different tumours were imaged in 18 rats. 1 rat failed and 3 tumours failed the biological criteria described in the preceding paragraph 5.5. The remaining 26 tumours in 17 rats were homogenous and had a massive non-necrotic interior. The average polarisation of $^{13}$C$_1$-pyruvate at the time of injection was 21.2±2.9% (mean ±SD) and the pH was 8.08±0.14 (mean ±SD).

FIG. 1 displays a typical set of images of one imaged rat with (1) the proton reference image, wherein the arrows indicate the tumour locations, (2) the $^{13}$C-pyruvate image, (3) the $^{13}$C-lactate image (4) the $^{13}$C-alanine image (5) the $^{13}$C-lactate image corrected for $^{13}$C-pyruvate and (6) the $^{13}$C-lactate image corrected for $^{13}$C-alanine. Images (2) to (6) are fused with the proton reference image.

Figure 2:
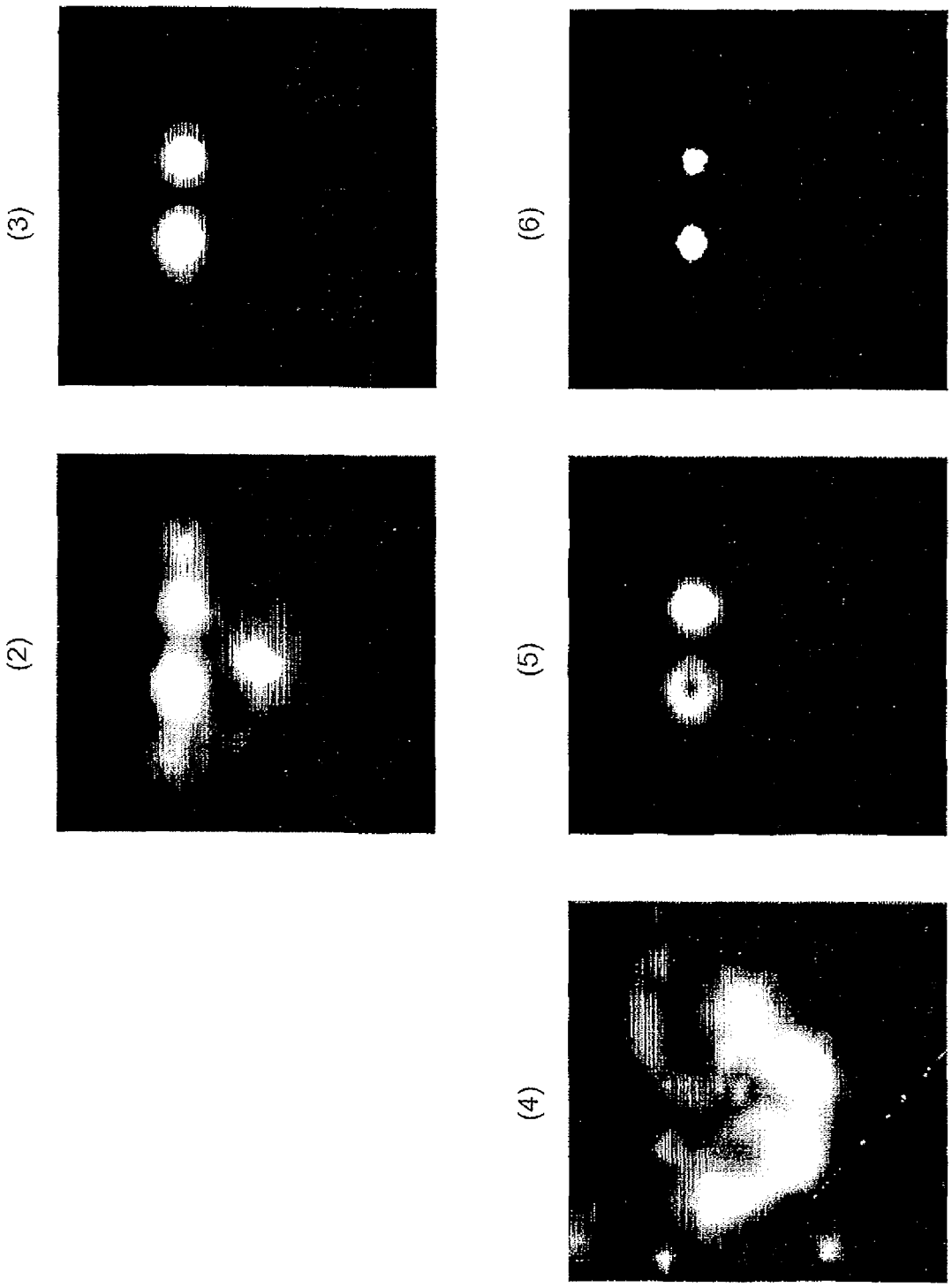
FIG. 2 displays the same set of images, however with images (2) to (6) which are not fused with the anatomical proton image.

FIG. 2 displays the same set of images, however with images (2) to (6) which are not fused with the anatomical proton image.

As a result, tumour location is indicated by a high pyruvate signal (2), due to high metabolic activity. However the lactate signal (3) ultimately identifies the correct location of the tumour. Alanine is visible in the skeletal muscle and is absent in the tumour tissue (4). The pyruvate and alanine corrected lactate images (5) and (6) result in an excellent contrast for the tumour as well.

It was thus demonstrated that the tumour location in the metabolic images is indicated by a high lactate signal, a high lactate signal corrected for pyruvate and a high lactate signal corrected for alanine.

The analysis of the metabolic $^{13}$C-MR images revealed a metabolic contrast in the tumour area in 24 out of 26 tumours for the lactate signal
26 out of 26 tumours for the lactate signal, pyruvate corrected (5.5, a))
26 out of 26 tumours for the lactate signal, alanine corrected (5.5, b))

The overall rate of success for this study was 26 out of 26, or 100%.

With this study, it was demonstrated that the hyperpolarised $^{13}$C$_1$-pyruvate reach the region of interest (tumour) in a time period which makes it possible to image the compound, that the compound and its metabolites can be imaged and that metabolic contrast can be obtained.

What is claimed is:

1. A method for producing a liquid composition comprising hyperpolarised $^{13}$C-pyruvate said method comprising a) forming a liquid mixture comprising a radical of formula (I), $^{13}$C-pyruvic acid and/or $^{13}$C-pyruvate and freezing the mixture;

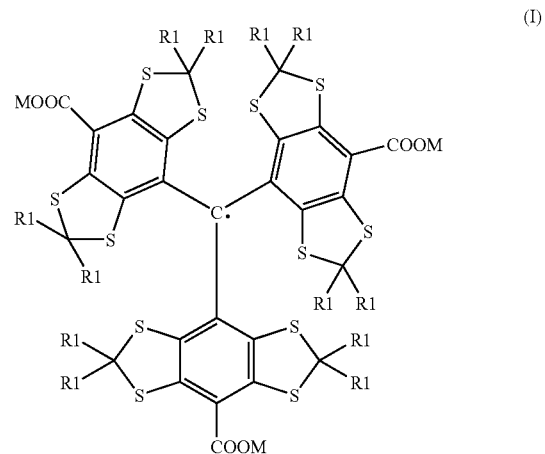

where
M represents hydrogen or one equivalent of a cation; and
R1 which is the same or different represents a straight chain or branched hydroxylated and/or alkoxylated $C_1$-$C_4$-hydrocarbon group b) enhancing the $^{13}$C nuclear polarisation of pyruvic acid and/or pyruvate in the mixture via DNP;

c) adding a buffer and a base to the frozen mixture to dissolve it and to convert the $^{13}$C-pyruvic acid into a $^{13}$C-pyruvate to obtain a liquid composition or, when only $^{13}$C-pyruvate is used in step a), adding a buffer to the frozen mixture to dissolve it to obtain a liquid composition, wherein the buffer is selected from the group consisting of phosphate buffer, ACES, PIPES, imidazole/HCI, BES, MOPS, HEPES, TES, TRIS, HEPPS and TRICIN; and d) optionally removing the radical and/or reaction products thereof from the liquid composition.

2. A method according to claim 1 wherein the radical is a radical of formula (I) where M represents hydrogen or one equivalent of a physiologically tolerable cation and R1 is the same or different and represents hydroxymethyl, hydroxyethyl or R1 is the same or different and represents a straight chain or branched alkoxylated $C_1$-$C_4$-hydrocarbon group carrying a terminal hydroxyl group or R1 is the same or different and represents a straight chain or branched alkoxylated $C_1$-$C_4$-hydrocarbon group.

3. A method according to claim 2 wherein R1 is the same and represents a straight chain or branched alkoxylated $C_1$-$C_4$-hydrocarbon group, preferably methoxy, —CH$_2$—OCH$_3$, —CH$_2$—OC$_2$H$_5$ or —CH$_2$—CH$_2$—OCH$_3$.

4. A method according to claim 1 wherein at least one of $^{13}$C-pyuric acid and $^{13}$C-pyruvate is isotopically enriched at the C1-position, at the C2-position, at the C3-position, at the C1- and the C2-position, at the C1- and the C3-position, at the C2- and the C3-position or at the C1-, C2- and the C3-position.

5. A method according to claim 1 wherein the isotopic enrichment of $^{13}$C-pyuric acid and/or $^{13}$C-pyruvate is at least 75%.

6. A method according to claim 1 wherein $^{13}$C-pyuric acid is used in step a) and wherein in step c) the buffer and the base are combined in one solution.

7. A method according to claim 1 wherein $^{13}$C-pyuric acid is used in step a) and the base is NaOH.

8. A method according to claim 1 wherein step d) is mandatory.

9. A method according to claim 8 for the production of a composition for use as an imaging agent for in vivo MR imaging of a human or non-human animal body.

10. The method of claim 1 wherein the buffer is selected from the group consisting of phosphate buffer and TRIS.

11. The method of claim 10 wherein $^{13}$C-pyuric acid is used in step a) and the base is NaOH.

12. The method of claim 10 wherein $^{13}$C-pyuric acid is used in step a) and wherein in step c) the buffer and the base are combined in one solution.

* * * * *